United States Patent [19]

Cerwin

[11] Patent Number: 4,458,682

[45] Date of Patent: Jul. 10, 1984

[54] NON-METALLIC, BIO-COMPATIBLE HEMOSTATIC CLIPS (RING LOCK CLIPS)

[75] Inventor: Robert J. Cerwin, Pittstown, N.J.

[73] Assignee: Ethicon, Inc., Somerville, N.J.

[21] Appl. No.: 404,261

[22] Filed: Aug. 2, 1982

[51] Int. Cl.³ .................. A61B 17/12; A61B 17/00
[52] U.S. Cl. .................................. 128/326; 128/346; 128/325
[58] Field of Search ............ 128/325, 326, 346, 303 A

[56] References Cited

U.S. PATENT DOCUMENTS

| | | | |
|---|---|---|---|
| 1,630,031 | 5/1927 | Rodgers | 128/346 |
| 1,750,654 | 3/1930 | Wappler | 128/346 |
| 3,150,666 | 9/1964 | Auerbach | 128/326 |
| 3,616,497 | 11/1971 | Esposito, Jr. | 128/346 |

Primary Examiner—C. Fred Rosenbaum
Assistant Examiner—C. W. Shedd
Attorney, Agent, or Firm—Robert L. Minier

[57] ABSTRACT

A sterile hemostatic clip for occluding vessels. The clip comprises a pair of diverging leg members and a ring member. The ring member is placed over the hinge portion of the clip and slides along the legs to occlude a vessel placed between the leg members.

5 Claims, 6 Drawing Figures

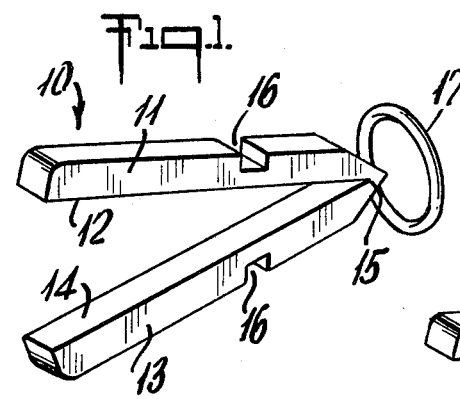
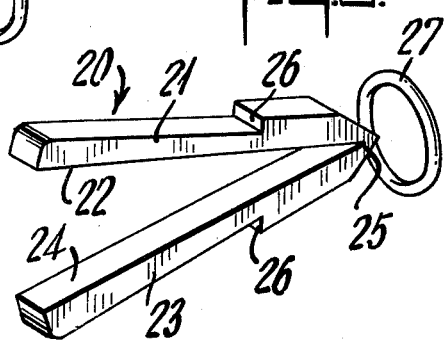
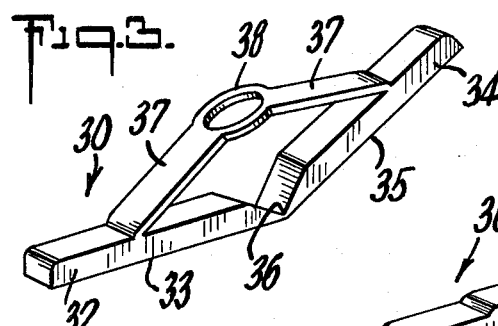
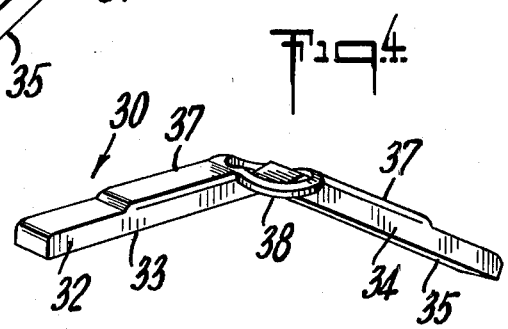
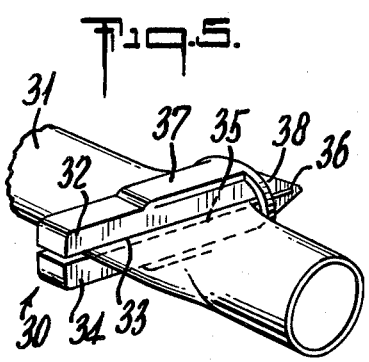

NON-METALLIC, BIO-COMPATIBLE HEMOSTATIC CLIPS (RING LOCK CLIPS)

The present invention relates to hemostatic clips and more particularly to hemostatic clips fabricated from bio-compatible polymeric materials which may be absorbable or non-absorbable in body tissue.

BACKGROUND OF THE INVENTION

In many surgical procedures, it is often necessary to ligate a plurality of vessels within the surgical site. The vessels may be severed downstream of the ligated portion. In some instances, the vessels may be ligated in spaced apart areas and the portion of the vessel between the ligations removed. The purpose of ligating vessels is to maintain the surgical site free from an excess of blood and reduce blood loss in the patient. Also, in certain surgical procedures where tumors and the like are to be removed, the tumor or organ may have to be separated from certain vessels. Before separating, the vessels are ligated. Once a blood vessel is completely shut off, hemostasis, that is, the natural closing of the end of the vessel so as to stop blood flow, will occur in several days depending on the vessel. The body, in the meantime, will continue to allow blood flow around the ligated area through appropriate capillaries and secondary vessels with the natural physiological function of the body enlarging these bypass vessels until adequate blood flow is obtained. Hence, when ligating the vessel, there should be positive stoppage of the blood flow in the main vessel. Failure to provide complete stoppage may cause blood loss in the patient and may also disrupt the natural hemostatis and concurrent manufacture of new passages for blood flow in the patient.

In the past, the closing of the vessel was usually accomplished using sutures; that is, filaments or threads which the doctor tied around the vessel to be closed. This is a time-consuming process and one wherein positive closure of the vessel is not always accomplished. In recent years, hemostatic clips have replaced ligatures in surgical procedures to close blood vessels and other fluid ducts. Very often, these hemostatic clips are narrow U or V shaped strips formed of tantalum or stainless steel which are capable of being deformed and possess sufficient strength to retain the deformation when clamped about a blood vessel. Recently, clips have been produced from various types of bio-compatible polymeric materials which are absorbable or non-absorbable in body tissue. Representative hemostatic clips made from polymeric materials are more fully described in co-pending commonly assigned U.S. patent application Ser. Nos. 276,131 filed June 22, 1981, 282,165 filed July 31, 1981, and (ETH 532).

The hemostatic clips should be constructed so that in use they positively lock the vessel closed. The clip should not be able to be moved or disrupted by the surgeon working in the operative cavity either with an instrument or by a sponge or the like. Also, the clip should be constructed so that it may be made of virtually any type of polymeric material whether it be absorbable or non-absorbable, and whether the polymer be resilient or non-resilient, deformable or non-deformable, etc. The clip should be simple to manipulate and handle by both the nurse and the surgeon and preferably should be simple and inexpensive to manufacture.

What we have discovered is an improved ligating clip structure which allows the clip to be made from substantially non-resilient and non-deformable material as well as from resilient and deformable materials. Our new configuration produces a clip which positively closes a blood vessel for a sufficient period of time to provide hemostasis and make a suitable hemostatic clip. Our clip configuration in the closed position is such that it is relatively inmovable if inadvertently hit by an instrument or sponge or the like. Our new clip is easy to manufacture by simple molding techniques well known in the art.

SUMMARY OF THE PRESENT INVENTION

A sterile hemostatic clip for use in occluding vessels comprising a pair of diverging leg members connected at their proximal end by a hinge portion. The hinge portion may be resilient or non-resilient depending on the material from which the clip is made. The leg members each have a vessel clamping surface disposed so that they face each other when the clip is in the closed position. The leg members each have a vessel clamping surface disposed so that they face each other when the clip is in the closed position. The clip includes a ring member adapted to slip over the hinge portion and encircle and engage the outer surfaces of the leg members and urge the leg members together. The vessel to be occluded is placed between the leg members so that the vessel clamping surfaces of the leg members contact the vessel to be occluded. The ring member slides over and engages the outer surfaces of the leg members and locks the legs together to occlude the vessel. In certain embodiments of the present invention, the ring is locked in place to the leg members by appropriate indentations in the outer surface of the leg members. In other embodiments of the clip of the present invention, the ring is placed over a raised portion on the outer surface of the leg members to lock the legs together. In some embodiments of the present invention, the ring member may be attached to one or both leg members so that the clip may be molded in a single operation.

BRIEF DESCRIPTION OF THE DRAWINGS

The present invention will be more fully described in conjunction with the accompanying drawings wherein:

FIG. 1 is an enlarged perspective view of a clip of the present invention in the open position;

FIG. 2 is an enlarged perspective view of another embodiment of a clip of the present invention in the open position;

FIG. 3 is an enlarged perspective view of yet another embodiment of a clip of the present invention in the open position;

FIG. 4 is an enlarged perspective view of the clip shown in FIG. 3 starting to be closed;

FIG. 5 is a perspective view of the clip of FIGS. 3 and 4 in a closed position occluding a vessel; and FIG. 6 is a side view and partial cross section showing an instrument for applying a clip of the present invention.

DETAILED DESCRIPTION OF THE DRAWINGS

Referring to the drawings in FIG. 1 there is shown a clip 10 of the present invention in the open position. The clip comprises a first leg member 11 having a body portion with a vessel clamping surface 12 and a second leg member 13 having a body portion with a vessel clamping surface 14. The vessel clamping surfaces of the leg members face each other. The first and the second leg members are connected at one end by a hinge portion 15. On the outer surface of each of the leg members is an indented area 16. The indented areas are spaced the same distance along the leg members from the hinge portion. The clip includes a ring member 17. In use, the ring member slips over the hinge portion of the leg members and is pushed along the outer surface of the leg members until it seats in the indented area to place the vessel clamping surfaces adjacent each other and occlude a vessel positioned between the vessel clamping surfaces.

In FIG. 2 there is shown another embodiment of the hemostatic clip of the present invention. In this embodiment, the clip 20 comprises a first leg member 21 having a vessel clamping surface 22 and a second leg member 23 having a vessel clamping surface 24. The leg members are connected at their proximal ends by a hinge portion 25. The outer surface of each leg member includes a raised area 26. In using the clip, the vessel clamping surfaces are placed on opposite sides of the vessel to be occluded and the ring member 27 urged over the hinge until it passes the raised areas on the outer surface of the leg members, closing the leg members about the vessel to occlude the vessel and lock the clip in the closed position.

In FIGS. 3, 4, and 5 there is shown another embodiment of a clip of the present invention. In this embodiment, FIG. 3 shows the clip 30 in the totally open position, FIG. 4 shows the clip 30 starting to be closed, and FIG. 5 shows the clip 30 closed about a blood vessel 31. In this embodiment, the clip comprises a first leg member 32 having a vessel clamping surface 33, and a second leg member 34 having a vessel clamping surface 35. The two leg members are connected at their proximal ends by a hinge portion 36. Connected to the outer surfaces of the leg members by bands 37 is a ring member 38. On closing the clip, the leg members are brought towards one another with their vessel clamping surfaces in face-to-face relationship and the ring brought about the hinge portion of the leg members. When the clip is fully closed as shown in FIG. 5, the vessel clamping surfaces occlude the vessel and the ring member has been passed over the hinge portion to a position abutting the bands to lock the clip in place.

FIG. 6 illustrates a forceps type ligating clip applier 50 comprising two handle members 51 and 52 crossing at a hinge point 53 and maintained in a normally open position by a spring 54. One handle extends beyond the hinge forming a jaw member 55 while the extension of the other handle also forms a corresponding jaw member 56. The jaws are identically designed and are constructed to place slight pressure on a clip 57 placed between the jaw members to hold the clip within the jaws. Positioned backward from the jaws and located so as not to interfere with the hinge portion 58 of the clip is a holder and plunger 59. At the open end of the holder the ring 61 of the clip is placed. In use, the jaw members with the clip in place are positioned over the vessel to be occluded with the vessel clamping surfaces of the leg members on opposite sides of the vessel. The handles of the forceps type instrument are compressed to close the leg members about the vessel. Simultaneously, the plunger is pushed forwardly by member 63 toward the jaws and positions the ring over the hinge portion of the clip to occlude the vessel. The jaws are released and the instrument removed and the clip remains in the closed position occluding blood vessel.

The clips of the present invention may be constructed in various sizes according to their intended function. Hemostatic clips are usually less than 6 millimeters in length and 1½ millimeters in width and have a vessel clamping surface of about 3 millimeters in length. The dimensions of the clip may be reduced by about 50% for certain applications in microsurgery. Larger clips for special hemostatic applications may be double the size of typical hemostatic clip. The various sizes of the clips are preferably matched with individual appliers having jaws tailored to the size of the clip for best performance.

The clips of the present invention are most conveniently molded of biologically acceptable polymeric materials which may be absorbable or non-absorbable in body tissue. Preferred absorbable polymers and copolymers include those of glycolide, lactide and poly(p)dioxanone. Preferred non-absorbable polymers include nylon, polyester and polypropylene. All these materials have been demonstrated to be biologically acceptable when used as sutures or other implantable medical devices.

The clips of the present invention may be sterilized by techniques well known in the art generally depending on the material of which the clip is made. These techniques include heat or steam sterilization, radiation sterilization such as cobalt irradiation or electron beam, ethylene oxide sterilization, and the like.

The clips of the present invention may be easily and economically manufactured by injection molding or other suitable techniques well known in the art.

What is claimed is:

1. A sterile hemostatic clip for use in occluding a vessel, said clip comprising a pair of diverging leg members connected at their proximal end by a resilient hinge portion, each leg member has a vessel clamping surface, the vessel clamping surfaces of the leg members face each other when the clip is in a closed position, a ring member adapted to pass over said hinge portion and urge the leg members together so that the vessel clamping surfaces are substantially parallel to occlude a vessel placed between said leg members and means associated with said leg members to lock said ring member in place when said vessel has been occluded.

2. A sterile hemostatic clip according to claim 1 wherein the means for locking the ring member in place comprises an indentation placed in the outer surface of a leg member.

3. A sterile hemostatic clip according to claim 1 wherein the ring member is attached to at least one of the leg members when the clip is in the open position.

4. A sterile hemostatic clip according to claim 1 made from an absorbable polymeric material.

5. A sterile hemostatic clip according to claim 4 where the absorbable polymeric material is a copolymer of lactide and glycolide.

* * * * *